(12) United States Patent
Yanni et al.

(10) Patent No.: US 12,158,460 B2
(45) Date of Patent: Dec. 3, 2024

(54) ADAPTIVE SENSOR FILTERING

(71) Applicant: INVENSENSE, INC., San Jose, CA (US)

(72) Inventors: Mamdouh Yanni, Brentwood, CA (US); Eiji Iwatsuki, San Jose, CA (US)

(73) Assignee: InvenSense, Inc., San Jose, CA (US)

( * ) Notice: Subject to any disclaimer, the term of this patent is extended or adjusted under 35 U.S.C. 154(b) by 262 days.

(21) Appl. No.: 17/592,800

(22) Filed: Feb. 4, 2022

(65) Prior Publication Data

US 2022/0252567 A1 Aug. 11, 2022

Related U.S. Application Data

(60) Provisional application No. 63/146,548, filed on Feb. 5, 2021.

(51) Int. Cl.
*G01N 33/00* (2006.01)
*G01K 7/42* (2006.01)

(52) U.S. Cl.
CPC ........... *G01N 33/0059* (2013.01); *G01K 7/42* (2013.01); *G01N 33/0031* (2013.01); *G01N 33/004* (2013.01); *G01N 33/007* (2013.01); *G01N 33/0073* (2013.01)

(58) Field of Classification Search
CPC ...... G01K 2201/00; G01K 7/42; G01N 25/18; G01N 33/0006; G01N 33/0031; G01N 33/004; G01N 33/0059; G01N 33/007; G01N 33/0073; G01N 33/0027; G01N 33/0036; G01N 33/0009; G01N 27/18; G01N 33/0004; G01N 27/4163; G01N 27/123; G01N 27/046; G01N 29/326; G01N 21/274; G01N 21/93; G01N 27/3274; G01N 30/8603; G01N 30/8624; G01N 2201/121; G01N 2201/1211; G01D 18/008

See application file for complete search history.

(56) References Cited

U.S. PATENT DOCUMENTS

| | | | | |
|---|---|---|---|---|
| 2003/0202654 | A1* | 10/2003 | Xiong | H04M 9/082 |
| | | | | 379/406.01 |
| 2008/0260141 | A1* | 10/2008 | Givens | H04M 9/082 |
| | | | | 379/406.08 |
| 2020/0333308 | A1 | 10/2020 | Billat et al. | |

FOREIGN PATENT DOCUMENTS

| | | | | |
|---|---|---|---|---|
| CN | 116802486 A | 9/2023 | | |
| WO | 2019040942 A1 | 2/2019 | | |
| WO | WO-2019065127 A1 * | 4/2019 | ........... | G01N 27/122 |

OTHER PUBLICATIONS

PCT/US2022/015253, International Searching Authority, International Search Report and Written Opinion, May 13, 2022.

* cited by examiner

*Primary Examiner* — John Fitzgerald
*Assistant Examiner* — Truong D Phan

(57) ABSTRACT

Environmental conditions affecting a sensor having a thermal coefficient are compensated by applying an adaptive filter to an environmental condition reference signal. The resulting adaptive cancellation signal may be used to provide feedback control to a first heating element.

16 Claims, 5 Drawing Sheets

ADAPTIVE SENSOR FILTERING

CROSS-REFERENCE TO RELATED APPLICATIONS

This application claims priority from and benefit of U.S. Provisional Patent Application Ser. No. 63/146,548, filed Feb. 5, 2021, entitled "ADAPTIVE FILTERING ARCHITECTURE FOR GAS SENSOR," which is assigned to the assignee hereof, and is incorporated by reference in its entirety.

FIELD OF THE PRESENT DISCLOSURE

This disclosure generally relates to the calibration of sensors and more specifically to the compensation of offset, sensitivity and drift in a sensor relying on the principal of thermal conductivity of an air transport mechanism.

BACKGROUND

The development of microelectromechanical systems (MEMS) has enabled the incorporation of a wide variety of sensors into devices, such as cell phones, laptops, tablets, gaming devices and other portable, electronic devices as well as stationary applications. In the context of this disclosure, MEMS-based sensors may also be used to measure or detect the presence of a gas in an ambient environment based on thermal conductivity. For example, a MEMS-based sensor can be employed in a heating, ventilation and air conditioning (HVAC) system to sense and optimize carbon dioxide content within an enclosed building. Generally, a reference sample and a detector sample are heated with corresponding thermistors measuring the transfer of heat across the samples. Since the resistance of the thermistors changes in response to the composition of gas in the sample, comparing the output of the thermistors allows the gas concentration in the sample to be determined. Although such techniques provide the ability to detect a wide variety of gases, thermal conductivity sensors can be sensitive to ambient environmental conditions, including temperature, humidity and pressure. Notably, ambient temperature can perturb gas concentration measurement by a factor of up to 400. Although less severe, humidity can impact measurements by a factor of up to 40, while pressure changes can also significantly degrade accuracy.

Attempts to compensate for the sensitivity of thermal conductivity sensors to environmental conditions have included techniques that provide controlled temperature and humidity. Unfortunately, this significantly limits the potential applications. Other approaches include careful characterization of the sensor under different environmental conditions to provide suitable calibration when those conditions are experienced. Although improvements in accuracy can be obtained, these techniques require time-consuming and expensive training regimens to provide the proper characterization. Further, the response of thermistors or other sensing elements can change over time and therefore require retraining to maintain accuracy, which is either laborious or practically infeasible.

Accordingly, it would be desirable to provide systems and methods to allow usage of a thermal conductivity sensor to measure gas concentration without requiring controlled environmental conditions or offline calibration to accommodate different environmental disturbances. Likewise, it would be desirable to reduce the need to calibrate a thermal conductivity sensor over a range of environmental conditions. Still further, it would be desirable to provide systems and methods for thermal conductivity sensors that accommodate changes in performance over time. As will be described in the material that follow, the techniques of this disclosure satisfy these and other needs.

SUMMARY

As will be described in detail below, this disclosure includes a method for compensating environmental conditions affecting a sensor having a thermal coefficient. The method involves obtaining an input sensor signal, obtaining a first environmental condition reference signal, applying a first filter having a weight to the first environmental condition reference signal to provide a first adaptive cancellation signal, mixing the first adaptive cancellation signal with the input signal to provide a first compensated sensor signal, and providing feedback control to a first heating element based at least in part on the first adaptive cancellation signal. The weight of the first filter may be based at least in part on the first compensated sensor signal.

In one aspect, the first environmental condition reference signal may be a temperature, humidity and/or pressure signal.

In one aspect, a second filter having a weight may be applied to the first environmental condition reference signal to provide a second adaptive cancellation signal, such that the second adaptive cancellation signal may be mixed with the input sensor signal to provide a second compensated sensor signal. The weight of the second filter may be based at least in part on the second compensated sensor signal. Feedback control is provided to a second heating element based at least in part on the second adaptive cancellation signal.

In one aspect, the input sensor signal may be a differential signal obtained from a detector temperature sensor and a reference temperature sensor. The first heating element may drive the detector temperature sensor and the second heating element may drive the reference temperature sensor.

In one aspect, a second environmental condition reference signal may be obtained so that a third filter having a weight may be applied to the second environmental condition reference signal to provide a third adaptive cancellation signal. Correspondingly, the third adaptive cancellation signal may be mixed with the first compensated sensor signal to provide a first double compensated sensor signal. The weight of the third filter may be based at least in part on the first double compensated sensor signal. Feedback control may be provided to the first heating element by combining the first adaptive cancellation signal with the third adaptive cancellation signal.

In one aspect, the first environmental condition reference signal and second environmental reference signal may be a temperature, humidity and/or pressure signal.

In one aspect, a fourth filter having a weight may be applied to the second environmental condition reference signal to provide a fourth adaptive cancellation signal. The fourth adaptive cancellation signal may be mixed with the first compensated sensor signal to provide a second double compensated sensor signal, such that the weight of the fourth filter may be based at least in part on the second double compensated sensor signal. Feedback control may be provided to a second heating element based at least in part on the fourth adaptive cancellation signal.

In one aspect, multiple environmental condition reference signals may be obtained so that adaptive filters for each of the multiple environmental reference signals may be applied and feedback control may be provided to the first heating element based at least in part on an adaptive cancellation signal from each adaptive filter. The multiple environmental condition reference signals may be temperature, humidity and/or pressure signals. Additional adaptive filters for each of the multiple environmental reference signals may be applied to provide feedback control to a second heating element based at least in part on adaptive cancellation signal from each additional adaptive filter.

In one aspect, controlling the first heating element may involve converting the first adaptive cancellation signal from digital domain to an analog domain.

In one aspect, the sensor may be a gas detector, such as a carbon dioxide detector.

In one aspect, the first environmental condition reference signal may be a humidity sensor, such that the humidity sensor is configured to measure absolute humidity.

In one aspect, the humidity sensitivity of the reference temperature sensor may be adjusted.

In one aspect, the convergence of the first adaptive cancellation signal may be adapted.

In one aspect, controlling the heating element(s) may involve applying a deviation less than one millivolt.

In one aspect, the first and second heating elements are configured to maintain different nominal temperatures.

This disclosure also includes a sensor system having a first heating element, a first environmental condition sensor, an input sensor signal and an adaptive sensor filter module. The adaptive sensor filter module may be configured to obtain the input sensor signal, obtain a first environmental condition reference signal from the first environmental condition sensor, apply a first filter having a weight to the first environmental condition reference signal to provide a first adaptive cancellation signal, mix the first adaptive cancellation signal with the first environmental signal to provide a first compensated sensor signal and provide feedback control to the first heating element based at least in part on the first adaptive cancellation signal. The weight of the first filter may be based at least in part on the first compensated sensor signal.

In one aspect, the sensor system has a detector temperature sensor and a reference temperature sensor. The input sensor signal may be a differential signal from the detector temperature sensor and the reference temperature sensor.

In one aspect, the adaptive sensor filter module may be further configured to apply a second filter having a weight to the first environmental condition reference signal to provide a second adaptive cancellation signal, mix the second adaptive cancellation signal with the first environmental signal to provide a second compensated sensor signal and provide feedback control to a second heating element based at least in part on the second adaptive cancellation signal. The weight of the first filter may be based at least in part on the second compensated sensor signal and the first and second heating elements may be configured to each drive one of the detector temperature sensor and the reference temperature sensor.

In one aspect, the first environmental condition sensor may be a temperature sensor.

In one aspect, the sensor system may have multiple environmental condition sensors. Correspondingly, the adaptive sensor filter module may obtain multiple environmental condition reference signals, apply adaptive filters for each of the multiple environmental reference signals and provide feedback control to the first and second heating elements based at least in part on adaptive cancellation signals from each adaptive filter.

In one aspect, the multiple environmental condition reference signals may include temperature, humidity and pressure signals.

In one aspect, the reference temperature sensor may be adjusted to have equivalent humidity sensitivity with respect to the detector temperature sensor by coupling a parallel resistor.

DETAILED DESCRIPTION

Figure 1:
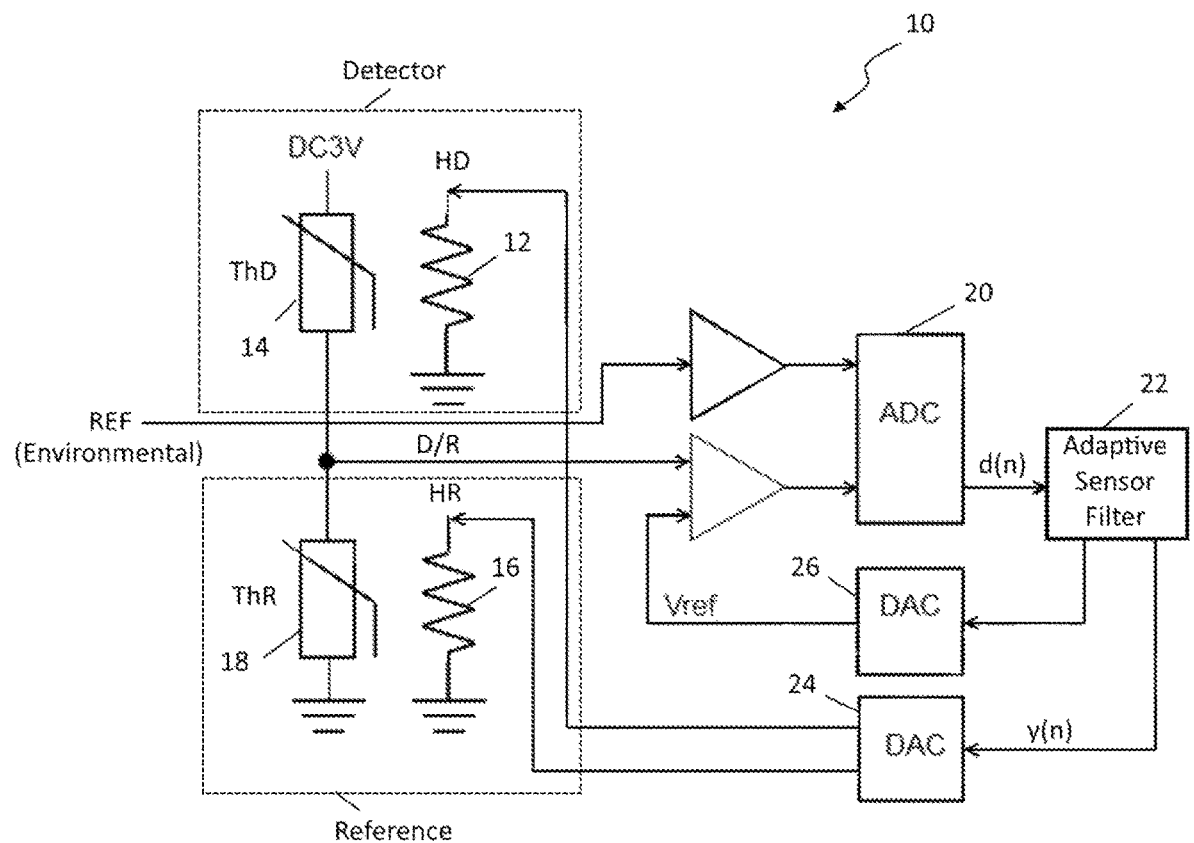
FIG. 1 is schematic diagram of a thermal conductivity sensor employing adaptive filtering according to an embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings or chip embodiments. These and similar directional terms should not be construed to limit the scope of the disclosure in any manner.

In this specification and in the claims, it will be understood that when an element is referred to as being "connected to" or "coupled to" another element, it can be directly connected or coupled to the other element or intervening elements may be present. In contrast, when an element is referred to as being "directly connected to" or "directly coupled to" another element, there are no intervening elements present.

Some portions of the detailed descriptions which follow are presented in terms of procedures, logic blocks, processing and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "accessing," "receiving," "sending," "using," "selecting," "determining," "normalizing," "multiplying," "averaging," "monitoring," "comparing," "applying," "updating," "measuring," "deriving" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the exemplary wireless communications devices may include components other than those shown, including well-known components such as a processor, memory and the like.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above. The non-transitory processor-readable data storage medium may form part of a computer program product, which may include packaging materials.

The non-transitory processor-readable storage medium may comprise random access memory (RAM) such as synchronous dynamic random-access memory (SDRAM), read only memory (ROM), non-volatile random-access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor. For example, a carrier wave may be employed to carry computer-readable electronic data such as those used in transmitting and receiving electronic mail or in accessing a network such as the Internet or a local area network (LAN). Of course, many modifications may be made to this configuration without departing from the scope or spirit of the claimed subject matter.

The various illustrative logical blocks, modules, circuits and instructions described in connection with the embodiments disclosed herein may be executed by one or more processors, such as one or more motion processing units (MPUs), digital signal processors (DSPs), general purpose microprocessors, application specific integrated circuits (ASICs), application specific instruction set processors (ASIPs), field programmable gate arrays (FPGAs), or other equivalent integrated or discrete logic circuitry. The term "processor," as used herein may refer to any of the foregoing structure or any other structure suitable for implementation of the techniques described herein. In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an MPU and a microprocessor, a plurality of microprocessors, one or more microprocessors in conjunction with an MPU core, or any other such configuration.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

According to this disclosure, systems and methods are provided to compensate for environmental conditions affecting a sensor having a thermal coefficient. To provide a context for the following discussion, FIG. 1 is a schematic diagram of a thermal conductivity sensor 10 that may be used to detect and/or measure the concentration of a gas within a sample for example. Although this embodiment is implemented with resistive heating elements and thermistor temperature sensors, other suitable components can be substituted as warranted. As shown, heating element 12 and thermistor 14 are disposed in a detector sample while heating element 16 and thermistor 18 are disposed in a reference sample. A differential signal D/R from thermistor 14 and thermistor 18 is fed to analog to digital converter (ADC) 20 along with a reference environmental signal REF, which may for example be an ambient temperature, humidity and/or pressure, amplified as indicated. Adaptive sensor filter module 22 then provides a feedback correction to heating element 12 and/or heating element 16 through digital to analog converter (DAC) 24. As will be appreciated, this architecture provides fine control over the heating element, such as at the µV level, and helps avoid saturation of the sensor.

Adaptive sensor filter module 22 also provides a reference voltage corresponding to the amount of gas detected through DAC 26. The feedback correction and the reference voltage can be modeled as a suitable order polynomial, such as a third degree or cubic polynomial, with the coefficients established as parameters during operation of adaptive sensor filter module 22. As will be discussed in further detail below, adaptive sensor filter module 22 employs one or more adaptive noise cancellation circuits to provide the feedback correction. The reference environmental signal can reflect any condition having an effect on the thermal coefficient of the sensor system. For example, ambient temperature has a substantial effect as noted above and in some embodiments, the reference environmental signal REF may be obtained from a suitable temperature sensor, such as a thermistor positioned on the sensor assembly. As will be appreciated, such a sensor may be positioned at a location that minimizes the influence of the heating elements so that a more accurate ambient temperature is measured. Further, as discussed below, other reference environmental signals may be used in the alternative or in addition to compensate for conditions such as humidity, pressure or any other condition affecting the thermal coefficients of system 10.

Adaptive sensor filter module 22 may be implemented in any suitable manner, such as through a processor which may be one or more microprocessors, central processing units (CPUs), or other processors to run software programs, which may be stored in memory which may be any combination of computer readable medium such as electronic memory or other storage medium such as hard disk, optical disk, etc., for use with the processor. Although described in the context of one or more sensors being MEMS based, the techniques of this disclosure may be applied to any sensor design or implementation. Correspondingly, adaptive sensor filter module 22 may be implemented as any suitable combination of hardware and software which includes, but is not limited to, application software, firmware, resident software, microcode, etc., and may take the form of a computer program product accessible from a computer-usable or computer-readable medium providing program code for use by or in connection with a computer or any instruction execution system or processing resources of sensor 10.

Figure 2:
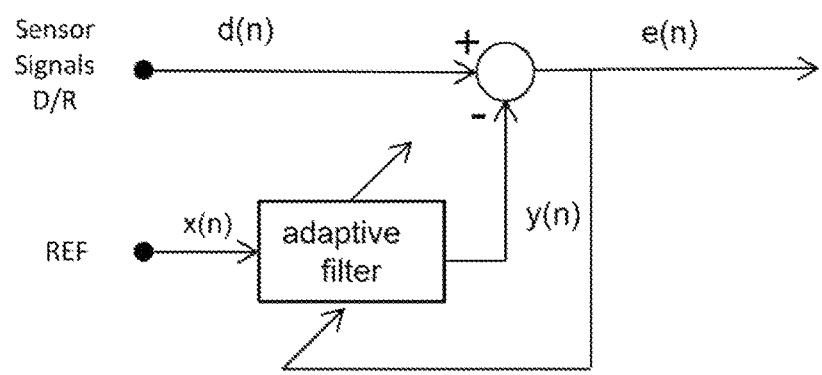
FIG. 2 is schematic diagram of an adaptive filter according to an embodiment.

An example of a suitable adaptive noise cancellation process is schematically depicted in FIG. 2 to reduce or eliminate any unwanted signal components. A sensor signal d(n) is provided as an input along with a reference signal x(n) such that the adaptive filter outputs the adaptive cancellation signal y(n). The adaptive cancellation signal y(n) can then be mixed with the input signal d(n) to provide a compensated sensor signal e(n). The weights of the adaptive filter are based at least in part on the compensated sensor signal e(n) as indicated, using system identification to accommodate offset, sensitivity and/or drift as well as any other unwanted signal components, essentially implementing an infinite impulse response filter. Filter weights (w) are updated by the following formula, shown in Equation 1, for each iteration:

$$w(n+1)=w(n)+2\mu e(n)x(n) \quad \text{Equation 1}$$

Here, x(n) is the input vector of time delayed input values and can be shown by Equation 2 as:

$$x(n)=[x(n)x(n-1)x(n-2)\ldots x(n-N+1)]^T \quad \text{Equation 2}$$

where:
  w(n) represents the coefficients of the adaptive FIR filter tap weight vector at time n; and
  µ is known as the step size, where if µ is too small the convergence on the optimal solution will take a long time and if µ is too large the adaptive filter becomes unstable and its output diverges.

In this adaptive filtering system, the objective is to produce a system output that is a best fit in the least squares sense (LMS) by feeding the system output back to the adaptive filter and adjusting the filter through an LMS adaptive algorithm to minimize total system output power (i.e., the system output serves as the error signal for the adaptive process (where the adaption is accomplished by the changed weights over time). Using the reference signal x(n) the adaptive filter will determine the correction y(n) needed for the sensor signals d(n). The correction y(n) may be applied to the signal lines that control the heater voltages of a sensor. The techniques of this disclosure reverse the typical feedforward architecture of adaptive noise cancellation to provide a feedback approach that allows heater compensation at a µV level as detailed below. Desirably, the sample rate of the filter may be chosen to be sufficiently high to keep performance within acceptable limits. Notably, the sensors of this disclosure are heavily impacted by three major errors, temperature, humidity and drift. Allowing these errors to go unchecked in real time, will effectively rail the sensor output, leading to saturation and the inability to record viable measurements. The adaptive noise cancellation architecture of this disclosure effectively identifies these correlated errors as noise and reduces or removes them via simultaneous automated system identification and compensation. As will be described, this is accomplished by directly controlling the amount of µV compensation applied to the heating elements to still provide viable sensor measurements having eliminated or at least reduced the disturbances that would otherwise render the sensor useless. For comparison, the conventional prior art methods employed within the field use offline "static" calibration which have been found to be ineffective in applications such as these. Due to significant drift and the impact of ambient environmental conditions, the calibration coefficients become useless in a short time frame. The techniques of this disclosure instead adopt online "dynamic" calibration that is continuously adapting to the current disturbances.

Figure 3:
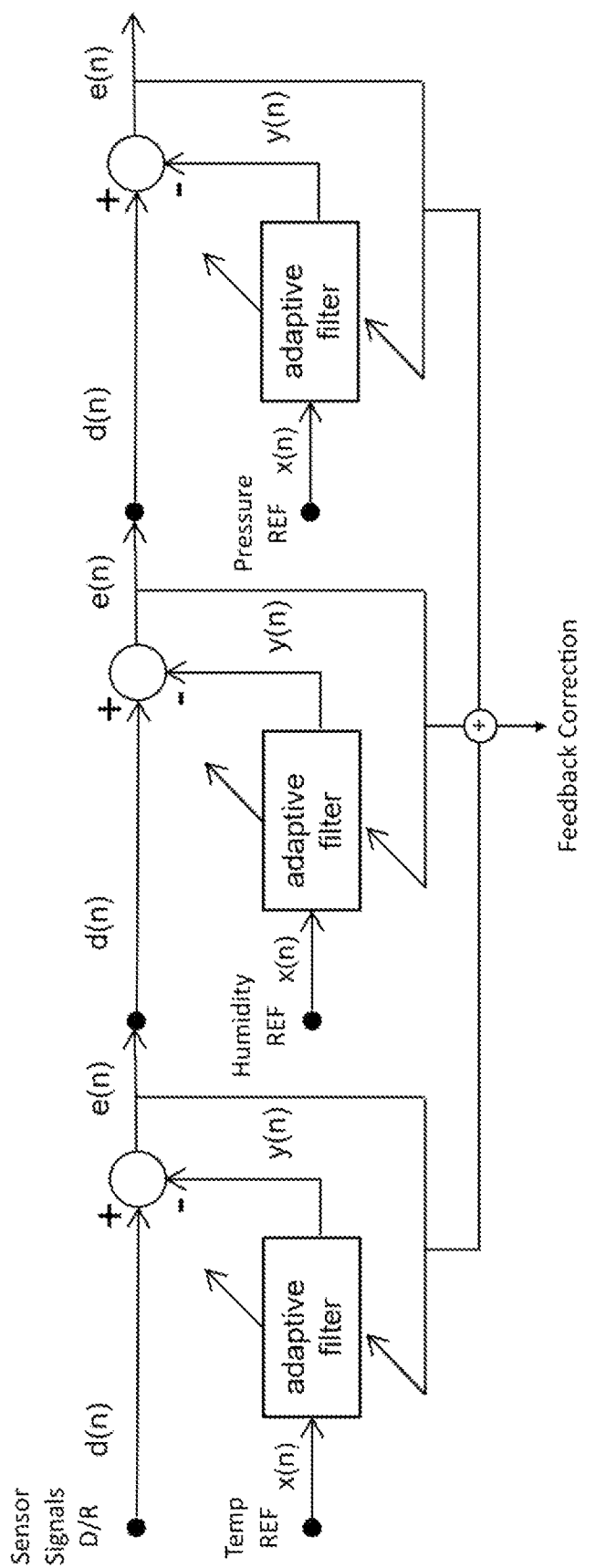
FIG. 3 is schematic diagram having sequential adaptive filtering for multiple environmental conditions according to an embodiment.

As discussed above, thermal conductivity sensors are significantly affected by ambient temperature and as a result, embodiments of this disclosure may utilize temperature as a suitable environmental condition reference signal as the input x(n) for the adaptive filter. However, other environmental conditions can also affect the operation of any sensor exhibiting a thermal coefficient and the techniques of this disclosure embody the use of any number of adaptive noise cancellation operations to help compensate for changes in these conditions, such as humidity and pressure. As one illustration, FIG. 3 schematically depicts a sensor architecture in which three cascading filters are employed to provide compensation for temperature, humidity and pressure. As shown, the compensated sensor signal e(n) from the preceding filter is then supplied as an input to the subsequent filter. In general, it is preferable to filter for the condition having the greater impact on sensor performance, namely temperature, before performing the subsequent humidity and pressure corrections. In other embodiments, one, two or more adaptive filters may be employed to compensate for any desired number of environmental conditions for which a reference signal can be supplied.

Figure 4:
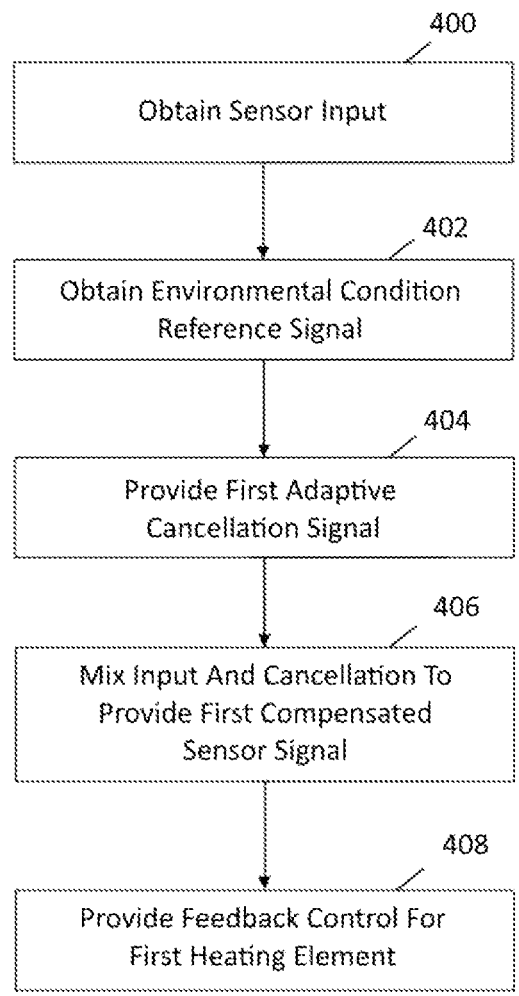
FIG. 4 is flowchart showing a routine that compensates for environmental conditions in a sensor having a thermal coefficient according to an embodiment.

To help illustrate aspects of compensating for environmental conditions affecting a sensor having a thermal coefficient, FIG. 4 depicts a flowchart showing a suitable routine according to one embodiment. Beginning with 400, a sensor signal reflecting the temperature differential between the detector sample and the reference sample is provided as an input. In 402, a first environmental condition reference signal is also used as an input. A first filter having a weight to the first environmental condition reference signal is used to provide a first adaptive cancellation signal in 404. In 406, the first adaptive cancellation signal is mixed with the input signal to provide a first compensated sensor signal, wherein the weight of the first filter is based at least in part on the first compensated sensor signal. In 408, feedback control is provided to a first heating element based at least in part on the first adaptive cancellation signal. As noted above, classical usage of adaptive noise cancellation is in a feedforward configuration but this disclosure employs a feedback approach that allows heater compensation at a µV level. For example, the first heating element may correspond to the detector heating element 12, but the correction could also be applied to the reference heating element 16 instead. As desired, additional adaptive noise cancellation operations may be performed. Notably, the above routine may be used with a second filter providing a second adaptive cancellation signal that is applied to the other heating element. These first and second adaptive cancellation signals may be based on the same environmental condition reference signal, such as the ambient temperature as measure by a sensor associated with the system as discussed above. Still further, each adaptive cancellation signal may be combined and used as feedback control for system 10, such as by adjusting the voltage driving heating elements 12 and/or 16. Desirably, simultaneous control is provided to the heating elements so that the sensors do not saturate when experiencing more than minor temperature deviations. Additionally, the above routines may be iterated for as many different environmental conditions as desired, including humidity and/or pressure.

Figure 5:
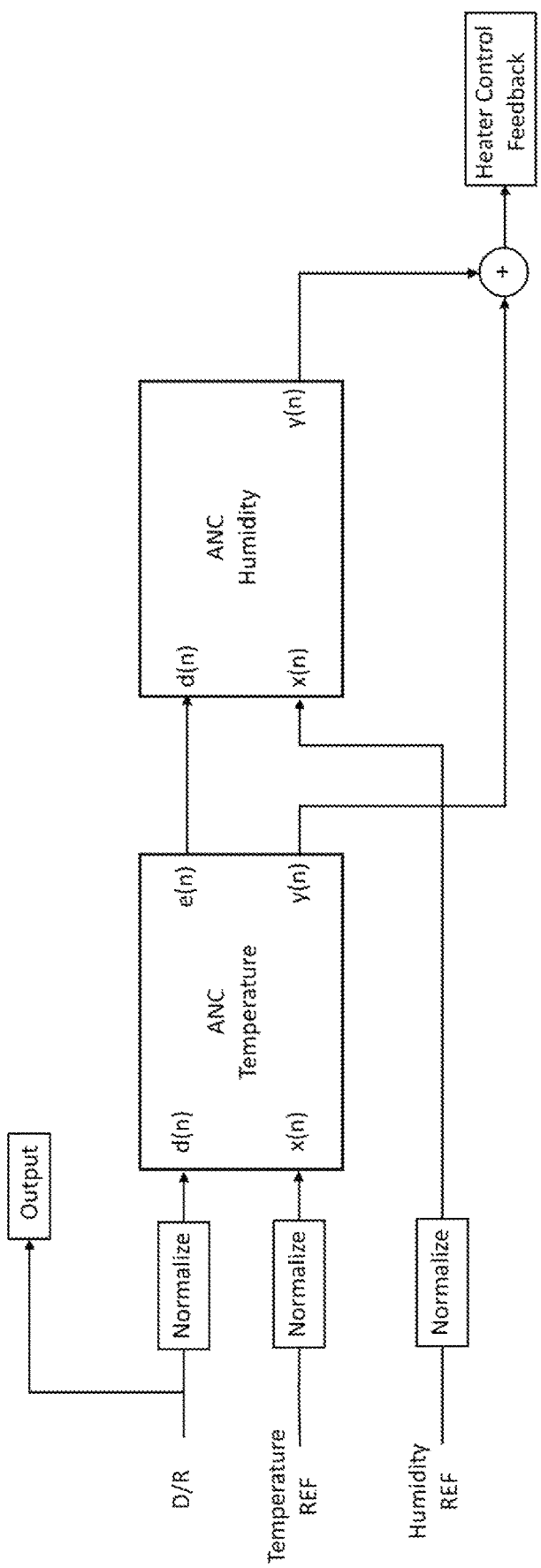
FIG. 5 is schematic diagram of a thermal conductivity sensor employing feedback heater control according to an embodiment.

As yet a further illustration of the techniques of this disclosure, FIG. 5 schematically depicts another embodiment configured to compensate for ambient temperature and humidity. As with the other embodiments discussed above, one primary input is the differential temperature measurement from the detector and reference samples, D/R. Here, the first filter is configured to compensate for the ambient temperature, so the other primary input is a reference temperature signal as indicated. The second filter receives a reference humidity signal as well as the compensated sensor signal from the first filter. The adaptive cancellation signals from both the first and second filters are combined and used to provide feedback control for the heaters of the system as discussed above. One characteristic of this architecture is that rather than using the compensated sensor signal from the second filter as the output for measuring the concentration of detected gas in a conventional feedforward technique, the feedback provided by the adaptive cancellation signals drives the input D/R to be inherently compensated for the input reference environmental conditions. Accordingly, the output taken directly from the measured differential D/R may be used to measure the detected gas concentration.

Figure 6:
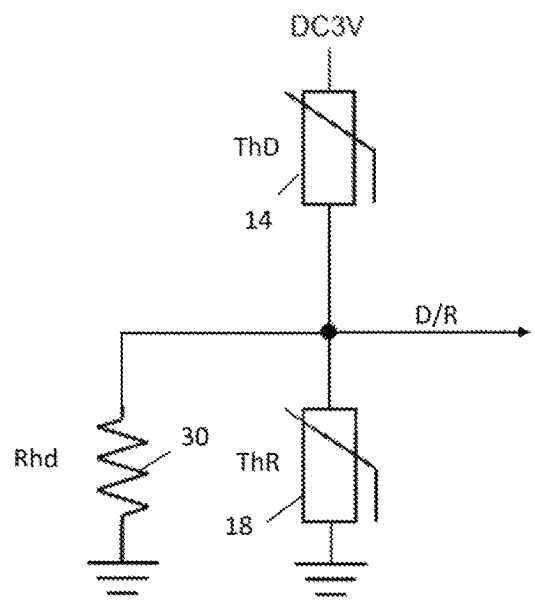
FIG. 6 is schematic diagram of a thermal conductivity sensor having adjusted humidity sensitivity according to an embodiment.
Figure 7:
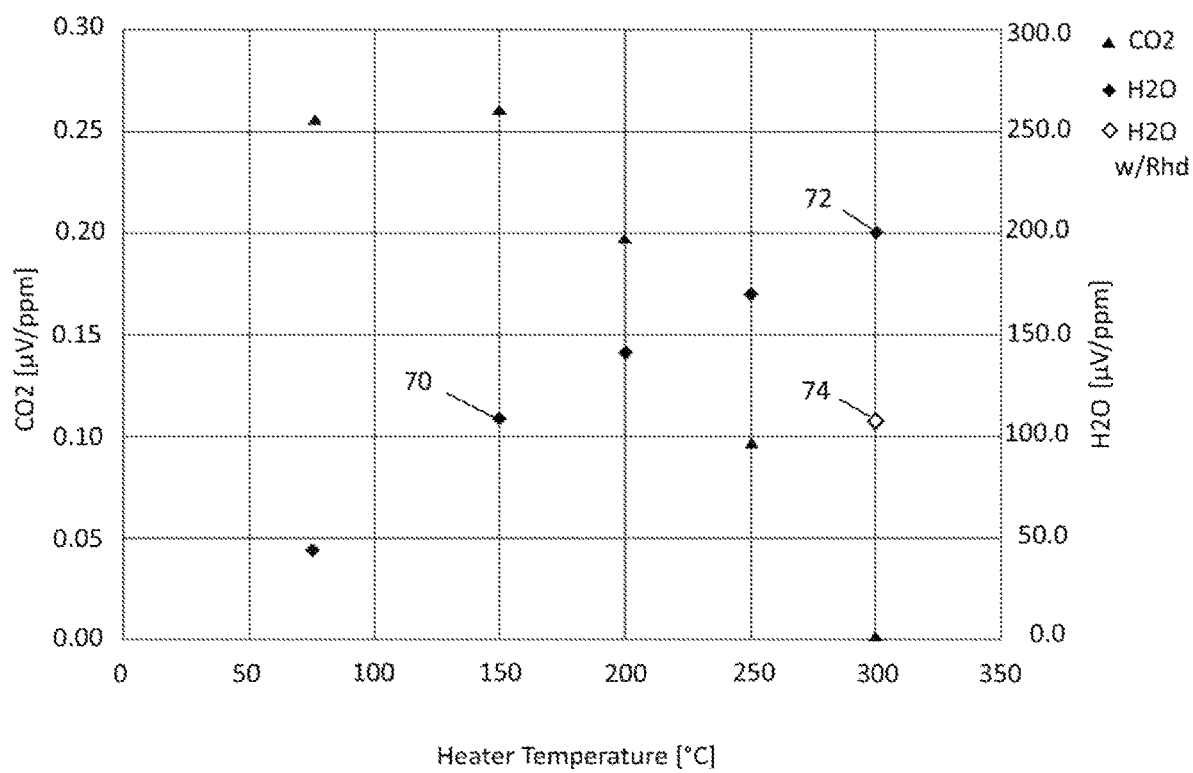
FIG. 7 is schematic diagram showing the relationship of measured carbon dioxide and humidity to temperature according to an embodiment.

In a further aspect, it has been found that using relative humidity as a reference environmental condition can cause inaccuracies in measurements of the sensor system due at least in part to different sensitivities of the reference and detector measurements. Accordingly, some embodiments of this disclosure employ absolute humidity when compensating for this environmental condition. In other embodiments, the sensitivities of the reference and detector may be adjusted so that they achieve similar performance, such as when a measurement of relative humidity is available so that an appropriate conversion may be applied. For example, FIG. 6 schematically depicts a differential thermistor pair such as employed in the embodiment of FIG. 2. As shown, connecting resistor Rhd 30 in parallel with the reference thermistor 18 reduces the sensitivity to humidity. The value of Rhd should be chosen to cause thermistor 18 to respond equivalently to thermistor 14 even though it operates at a different temperature. As an illustration, the following discussion is in the context of sensor system 10 configured to detect carbon dioxide. In such an embodiment, heating element 12 sets the detector sample to 150° C. and heating element 16 set the reference sample to 300° C. A plot of the measurement in µV for $CO_2$ and $H_2O$ (humidity) at different temperatures is shown in FIG. 7. As can be seen, the measured voltage for $CO_2$ at 300° C. is 0 meaning that the reference thermistor 18 is detecting only humidity, while the detector thermistor 14 operating at 150° C. is detecting both humidity and $CO_2$. Since the desired result is for the differential measurement D/R provided by the combination of thermistor 14 and thermistor 18 to reflect only $CO_2$, the $H_2O$ measurement from each thermistor should be the same. However, plot 70 shows the humidity measurement at 150° is not the same as plot 72 which shows the nominal humidity measurement at 300°. Correspondingly, resistor Rhd 30 should be connected in parallel with thermistor 18 to provide the humidity measurement shown by plot 74, which is equivalent to plot 70. Under this configuration, the influence of humidity on both detector thermistor 14 operating at 150° C. and reference thermistor 18 operating at 300° C. will be the same and the differential signal D/R will properly respond only to $CO_2$ concentration.

From the above discussion, it will be appreciated that the techniques of this disclosure employ adaptive filters in a feedback, rather than feedforward, architecture. Further, the use of adaptive filters automatically provides correction for sensor drift by compensating for the thermal coefficient offset of the sensor system and sensor response by compensating for the thermal coefficient sensitivity. During operation of the system, the adaptive filter(s) optimize the parameters for heater feedback control and reference voltage to reduce the disturbance contribution to the signals based on varying environmental conditions, including temperature, humidity and/or pressure. Because the gas sensor is very sensitive to changes, a slow convergence may be preferred to avoid hysteresis. During the initial operation, some time may be required for that adaptive filters to arrive at the appropriate parameters. However, the adaptive nature of the technique means that the system will automatically accommodate changes in sensor performance over time, such as may be cause by aging without requiring recalibration under controlled settings to recharacterize the sensors. Correspondingly, the techniques of this disclosure allow relatively inexpensive thermal differential sensors to accurately measure gas concentrations without requiring controlled environments which greatly increases the number of suitable applications.

Although the present invention has been described in accordance with the embodiments shown, one of ordinary skill in the art will readily recognize that there could be variations to the embodiments and those variations would be within the spirit and scope of the present invention. For example, although the above discussion has been provided in the context of detecting and measuring gasses, the techniques may be extended to any sensor using a thermal conductivity principle. Accordingly, many modifications may be made by one of ordinary skill in the art without departing from the spirit and scope of the present invention.

What is claimed is:

1. A method to compensate for environmental conditions affecting a sensor having a thermal coefficient comprising:
   driving a detector temperature sensor utilizing a first heating element;
   driving a reference temperature sensor utilizing a second heating element, wherein the detector temperature sensor and the reference temperature sensor form a differential thermistor pair;
   obtaining an input sensor signal, wherein the input sensor signal is a differential signal obtained from the detector temperature sensor and the reference temperature sensor;
   obtaining an environmental condition reference signal from an environmental condition sensor, wherein the environmental condition reference signal is a voltage representative of an environmental condition;
   utilizing the environmental condition reference signal as a first input to an adaptive filter;
   determining a compensated sensor signal, by comparing the input sensor signal with an adaptive cancellation signal which is output by the adaptive filter;
   utilizing the compensated sensor signal as a second input to the adaptive filter, wherein the compensated sensor signal provides feedback control to the adaptive filter;
   performing, with the adaptive filter, adaptive noise cancellation based on the compensated sensor signal and the environmental condition reference signal; and
   providing feedback control to the first heating element and the second heating element based on the adaptive cancellation signal.

2. The method of claim 1, wherein the environmental condition reference signal comprises at least one of temperature, humidity and pressure signals.

3. The method of claim 1, further comprising:
   obtaining multiple environmental condition reference signals;
   applying adaptive filters for each of the multiple environmental condition reference signals; and
   providing feedback control to the first heating element based at least in part on an adaptive cancellation signal from each adaptive filter.

4. The method of claim 3, wherein the multiple environmental condition reference signals each comprise one of temperature, humidity and pressure signals.

5. The method of claim 4, further comprising applying additional adaptive filters for each of the multiple environmental condition reference signals and providing feedback control to a second heating element based at least in part on adaptive cancellation signal from each additional adaptive filter.

6. The method of claim 1, wherein providing feedback control to the first heating element comprises converting the adaptive cancellation signal from digital domain to an analog domain.

7. The method of claim 1, wherein the detector temperature sensor comprises a gas detector.

8. The method of claim 7, wherein the detector temperature sensor comprises a carbon dioxide detector.

9. The method of claim 1, wherein detector temperature sensor comprises a humidity sensor and wherein the humidity sensor is configured to measure absolute humidity.

10. The method of claim 1, wherein controlling the first heating element comprises applying a deviation less than one millivolt.

11. The method of claim 1, wherein the first and second heating elements are configured to maintain different nominal temperatures.

12. A sensor system having:
   a first heating element;
   a second heating element;
   an environmental condition sensor;
   a detector temperature sensor, which is driven by the first heating element;
   a reference temperature sensor, which is driven by the second heating element; and
   an adaptive sensor filter module, wherein the sensor system is configured to:
      obtain an input sensor signal, wherein the input sensor signal is a differential signal obtained from the detector temperature sensor and the reference temperature sensor;
      obtain an environmental condition reference signal from the environmental condition sensor, wherein the environmental condition reference signal is a voltage representative of an environmental condition;
      utilize the environmental condition reference signal as a first input to the adaptive sensor filter module;
      determine a compensated sensor signal, by a comparison of the input sensor signal with an adaptive cancellation signal which is output by the adaptive sensor filter module;
      utilize the compensated sensor signal as a second input to the adaptive sensor filter module, wherein the compensated sensor signal provides feedback control to the adaptive sensor filter module;
      perform, with the adaptive sensor filter module, adaptive noise cancellation based on the compensated sensor signal and the environmental condition reference signal; and
      provide feedback control to the first heating element based on the adaptive cancellation signal.

13. The sensor system of claim 12, wherein the environmental condition sensor is a temperature sensor.

14. The sensor system of claim 12, further comprising multiple environmental condition sensors and wherein the sensor system is further configured to:
   obtain multiple environmental condition reference signals;
   apply adaptive filters for each of the multiple environmental condition reference signals; and provide feedback control to the first and second heating elements based at least in part on adaptive cancellation signals from each adaptive filter.

15. The sensor system of claim 14, wherein the multiple environmental condition reference signals each comprise one of temperature, humidity and pressure signals.

16. The sensor system of claim 1, wherein the reference temperature sensor is adjusted to have equivalent humidity sensitivity with respect to the detector temperature sensor by coupling a parallel resistor.

* * * * *